(12) United States Patent
Avrutov et al.

(10) Patent No.: US 6,806,373 B2
(45) Date of Patent: Oct. 19, 2004

(54) PROCESS FOR PREPARING LEFLUNOMIDE FORM I

(75) Inventors: Iiya Avrutov, Bat Hefer (IL); Neomi Gershon, Kfar Saba (IL); Judith Aronhime, Rechovot (IL)

(73) Assignee: Teva Pharmaceutical Industries Ltd., Petah Tigva (IL)

( * ) Notice: Subject to any disclaimer, the term of this patent is extended or adjusted under 35 U.S.C. 154(b) by 0 days.

(21) Appl. No.: 10/410,493

(22) Filed: Apr. 8, 2003

(65) Prior Publication Data

US 2003/0203952 A1 Oct. 30, 2003

Related U.S. Application Data

(62) Division of application No. 09/736,727, filed on Dec. 14, 2000, now Pat. No. 6,610,718.
(60) Provisional application No. 60/171,228, filed on Dec. 16, 1999, provisional application No. 60/202,416, filed on May 8, 2000, provisional application No. 60/171,237, filed on Dec. 16, 1999, and provisional application No. 60/182,647, filed on Feb. 15, 2000.

(51) Int. Cl.$^7$ ............................................. C07B 26/00
(52) U.S. Cl. ...................................................... 548/248
(58) Field of Search ......................................... 548/248

(56) References Cited

U.S. PATENT DOCUMENTS

| 4,284,786 A | 8/1981 | Kämmerer et al. |
| 6,060,494 A | 5/2000 | Faasch et al. |
| 6,221,891 B1 | 4/2001 | Faasch et al. |

FOREIGN PATENT DOCUMENTS

| AU | A-78870/98 | 2/1999 |
| EP | 0 903 345 | 3/1999 |

*Primary Examiner*—Joseph K. McKane
*Assistant Examiner*—Kamal Saeed
(74) *Attorney, Agent, or Firm*—Kenyon & Kenyon

(57) ABSTRACT

New leflunomide Form III is disclosed, along with processes for preparing it. The present invention also provides an economic process for preparing leflunomide Form II and a process for preparing leflunomide Form I from leflunomide Form III. Pharmaceutical compositions and dosage forms containing the new form and methods of using them for the treatment of rheumatoid arthritis are also disclosed.

6 Claims, 4 Drawing Sheets

PROCESS FOR PREPARING LEFLUNOMIDE FORM I

RELATED APPLICATION

This application is a division of U.S. patent application Ser. No. 09/736,727, filed Dec. 14, 2000 now U.S. Pat. No. 6,610,718 which claims the benefit under 35 U.S.C. §119(e) of U.S. Provisional Patent Application No. 60/171,228, filed Dec. 16, 1999, U.S. Provisional Patent Application No. 60/202,416, filed May 8, 2000, U.S. Provisional Patent Application No. 60/171,237, filed Dec. 16, 1999, and U.S. Provisional Patent Application No. 60/182,647, filed Feb. 15, 2000, all of which are incorporated herein by reference.

FIELD OF THE INVENTION

The present invention relates to a novel leflunomide Form III and to processes for making leflunomide Forms I, II and III.

BACKGROUND OF THE INVENTION

Leflunomide (5-methylisoxazole-4-carboxylic acid), having the formula 1:

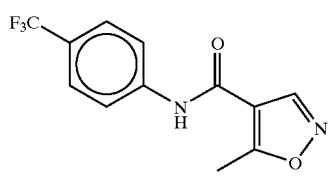

(I)

is an inhibitor of pyrimidine biosynthesis with antiproliferative activity and is approved in the United States for treatment of rheumatoid arthritis.

The present invention relates to polymorphic forms of leflunomide. Polymorphism is the property of some molecules to adopt more than one crystalline form in the solid state. A single molecule may give rise to a variety of solids having distinct physical properties that can be measured in a laboratory like its thermal behavior—e.g. melting point and differential scanning calorimetry ("DSC") thermogram—dissolution rate, flowability, X-ray diffraction pattern, infrared absorption spectrum and NMR spectrum. The differences in the physical properties of polymorphs result from the orientation and intermolecular interactions of adjacent molecules in the bulk solid. Accordingly, polymorphs are distinct solids sharing the same molecular formula which may yet have distinct advantageous and/or disadvantageous physical properties compared to other forms in the polymorph family.

One property of a pharmaceutical compound that can vary depending upon its polymorphic form is its rate of dissolution in aqueous solvent. The rate of dissolution can have therapeutic consequences since it can affect the rate that an orally administered pharmaceutical is delivered to the bloodstream of a patient. The rate of dissolution is also a consideration in formulating syrups, elixirs and other liquid medicaments. A more rapidly dissolving form facilitates production of these liquid pharmaceuticals.

U.S. Pat. No. 4,284,786 describes the preparation of leflunomide from 5-methylisoxazole-4-carboxylic acid and 4-trifluoromethylaniline. Leflunomide is obtained from the crude product of Examples a.1–a.7 of the '786 patent by recrystallization from toluene. The recrystallized product is reproducibly identified by its melting point at 166.5° C. U.S. Pat. No. 4,284,786 and the commonly-assigned co-pending U.S. Patent Application Publication No. 2002/0022646 are hereby incorporated by reference for their methods of preparing leflunomide.

According to Australian patent No. AU-A-78870/98, practice of the procedure of the '786 patent yields leflunomide Form I. The AU-A-78870/98 patent characterizes leflunomide Form I by its X-ray diffraction pattern, which is said to have strong peaks at 16.70, 18.90, 23.00, 23.65 and 29.05° at 2θ and weaker peaks at 8.25, 12.65, 15.00, 15.30, 18.35, 21.25, 22.15, 24.10, 24.65, 25.45, 26.65, 27.40, 28.00 and 28.30° at 2θ.

The AU-A-78870/98 patent further describes leflunomide Form II, which is asserted to be a previously unknown form. According to the AU-A-78870/98 patent, Form II is kinetically stable up to 40° C. and more readily dissolves in water than does Form I. Form II is characterized by its X-ray diffraction pattern and IR absorption spectrum. Form II is said to exhibit strong peaks in the powder X-ray diffraction pattern at 10.65, 14.20, 14.80, 16.10, 21.70, 23.15, 24.40, 24.85, 25.50, 25.85, 26.90 and 29.85° at 2θ and weaker peaks at 7.40, 9.80, 13.10, 15.45, 16.80, 20.70, 21.45, 22.80, 23.85, 27.25 and 28.95° at 2θ. The infrared absorption spectrum of Form II is said to have bands at 427, 484, 511, 592, 628, 672, 701, 733, 754, 763, 831, 852, 877, 894, 908, 940, 948, 960, 974, 1014, 1065, 1109, 1160, 1188, 1241, 1264, 1321, 1361, 1384, 1410, 1481, 1536, 1607, 1663, 1691, 1779, 1811, 3065, 3111, 3129, 3201, 3221, 3274, 3297, 3355, 3434 and 3442 cm$^{-1}$.

According to AU-A-78870/98, Form II may be obtained by suspending Form I in water or mixtures of water and $C_1$–$C_4$ alcohols, acetone or methyl ethyl ketone. The suspension may be heated to less than 40° C. to accelerate the conversion of Form I to Form II, which takes from 36–65 hours if the suspension is not heated. The Form I and II crystals are not completely dissolved during this process, even with heating, since leflunomide is poorly soluble in these solvents. The process must be monitored by analyzing samples to determine when the conversion is complete. This method is time-consuming because of the low transition rate of the polymorphs.

According to AU-A-78870/98, Form II may also be obtained by rapidly cooling a solution of leflunomide in a $C_1$–$C_4$ alcohol, acetone, methyl ethyl ketone, ethyl acetate, toluene or dichloromethane. Rapid cooling may be achieved by slowly introducing the solution into a cold vessel at a rate that does not warm the vessel to more than −10° C. or by spraying into a cold or evacuated chamber. Each method traps the molecules in kinetically favored Form II and each method requires special equipment or materials.

Heating or cooling can be an important factor in the cost of industrial production of pharmaceuticals. Shock cooling requires special equipment and an additional reactor, adding to the cost. The temperature of −10° C., which can be achieved by dissolving sodium chloride in ice water, is approximately the lower limit of temperatures that are obtainable without costly equipment or materials. It would be highly desirable to be able to crystallize leflunomide Form II at a temperature of −10° C. or above.

SUMMARY OF THE INVENTION

One objective of the present invention is to provide an economic process for preparing leflunomide Form II for use in pharmaceutical compositions. We have surprisingly found that leflunomide Form II may be obtained by precipitating leflunomide from a solution in selected polar solvents and mixtures of polar solvents and an "anti-solvent" without resorting to rapid cooling. Optional slow cooling to induce and maximize crystallization of leflunomide Form II may be conducted at temperatures generally above −10° C. Leflunomide Form II is thus obtained in good yield. Even in solvent systems wherein the yield of Form II is less than 50%, the unprecipitated leflunomide may be easily recovered and recycled.

The present invention also provides new leflunomide Form III. We have unexpectedly found that a novel form of leflunomide designated Form III is obtained by crystallizing leflunomide according to our process for crystallizing Form II from different solvent systems. Form III is obtained when the solvent is 2-pyrrolidone or a mixture of 2-pyrrolidone and water. It was also found that by heating Form III to about 60° C. under vacuum for an extended period of time it transformed into Form I.

DETAILED DESCRIPTION OF THE INVENTION

Figure 1:
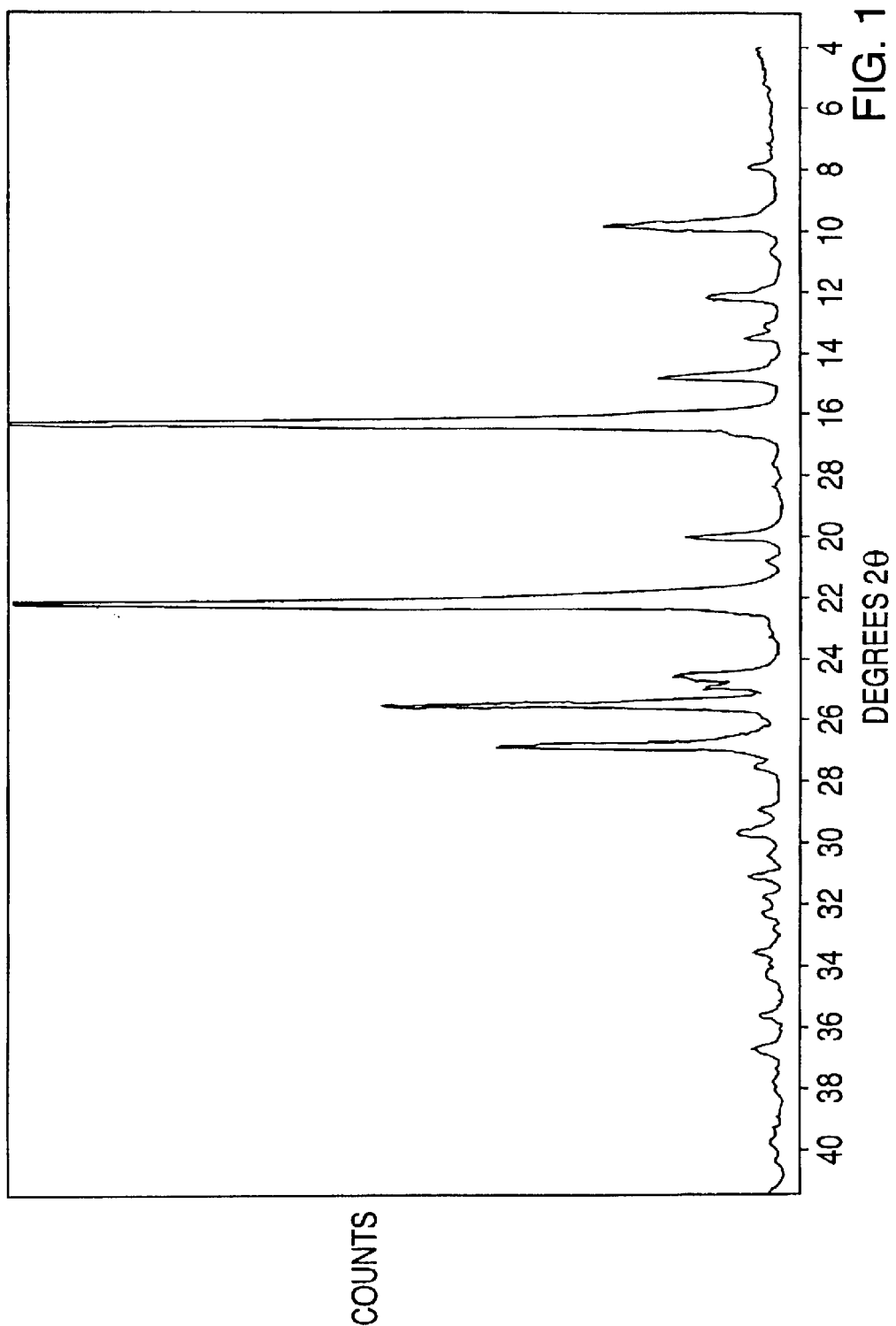
FIG. 1 is a characteristic powder X-ray diffraction pattern of leflunomide Form III.

The present invention provides novel Form III of leflunomide and processes for making leflunomide Forms I, II and III.

The process of making leflunomide Form II of the present invention is a crystallization procedure. The procedure may be conducted at ambient, elevated or reduced temperature. It is feasible using this process to obtain good yields of leflunomide Form II without cooling below −10° C. and preferably not below 0° C. More preferably, the process is conducted at ambient temperature of the laboratory or industrial facility. In response to a need for improved efficiency in the production of leflunomide Form II, which has desirable solubility properties in aqueous solution, we have discovered crystallization conditions that favor the selective crystallization of Form II in good yield and at economical temperatures for production.

Our process for making leflunomide Form II involves dissolving any form of leflunomide in a solvent, hereafter referred to as "the leflunomide solvent," to form a leflunomide solution and then crystalizing leflunomide under conditions that produce Form II. The crystals are then isolated by decanting, filtration, evaporation or any other conventional method that separates the crystals from most of the solvent. Following isolation, the crystals may optionally be washed and/or dried.

The leflunomide solution is made by dissolving any form of leflunomide in one of the leflunomide solvents, mixtures thereof or mixtures thereof with other solvents. The leflunomide may be chemically pure or impure and may be a single form of leflunomide or a mixture of forms. Preferably, the leflunomide is nearly chemically pure.

The leflunomide solvents of the present invention for crystallizing leflunomide Form II are dimethylsulfoxide ("DMSO"), 2-ethoxy ethanol, 1,3-dimethylimidazolin-2-one ("DMI"), acetone, isopropyl alcohol ("IPA"), 1,2-dimethoxyethane ("DME"), methanol ("MeOH"), dioxane, N,N-dimethyl formamide ("DMF") and ethyl acetate ("EtOAc").

The leflunomide may be dissolved in the leflunomide solvent at any practicable temperature, but typically it is dissolved at ambient or elevated temperature. Generally, the elevated temperature of the present invention can be as high as the reflux temperature of the solvent at ambient pressure, although a higher pressure, and a temperature up to the reflux temperature of the solvent at the higher pressure may also be used.

In the process for making leflunomide Form II of the present invention, crystallization may be induced either by addition of an "anti-solvent" or by a reduction in temperature to about −10° C. or above, or both. The leflunomide solution may be filtered before crystallization to remove any solid impurities from the leflunomide or to remove any undissolved leflunomide.

Anti-solvents of the present invention are water and $C_5$–$C_8$ alkanes that are liquid above 20° C., such as pentane and its branched and cyclic isomers, hexane and its branched and cyclic isomers, heptane and its branched and cyclic isomers and octane and its branched and cyclic isomers. The term "isomers" refers to molecules having the same number of carbon atoms. Cyclic isomers therefore will not necessarily have the same molecular formula or weight as the linear and branched isomers. Among the low molecular weight alkanes, the most preferred are the hexanes, in particular n-hexane, mixtures of hexanes and mixtures of hexanes and pentanes. The solvent:anti-solvent ratio may vary from 1:0.1 to 1:10, preferably from 1:0.15 to 1:3. Preferred solvents for use when crystallizing leflunomide Form II by addition of an anti-solvent are DMF, DMI and dioxane.

Crystallization of leflunomide Form II also may be induced by cooling to a temperature of not less than −10° C., preferably not less than 0° C. Special rapid, or "shock," cooling techniques and equipment are not required. Conventionally, the leflunomide solution may be cooled by cooling a vessel containing the solution with cold brine, circulating ice water or tap water, or by cessation of heating or any other conventional means. The preferred leflunomide solvents from which leflunomide may be induced to crystallize in Form II by conventional cooling are DMSO, DME and 2-ethoxyethanol.

Whether induced by addition of an anti-solvent or cooling, crystallization may be further promoted by addition of seed crystals of leflunomide Form II.

The leflunomide solution should be allowed to stand, with or without agitation, for about half an hour or more after the solution begins to thicken for a better yield.

In each embodiment of the process for making leflunomide Form II, the solvent is removed. The solvent may be removed by any conventional method, like decanting or filtering, preferably filtering. Unprecipitated leflunomide can be recovered by concentration of the mother liquor and harvesting a second crop of leflunomide Form II from the concentrate. Alternatively, the solvent can be evaporated and the residue combined with another batch of starting leflunomide.

The leflunomide Form II crystals obtained after removal of the solvent may be washed, e.g. with water, and dried at ambient temperature under vacuum. The resulting product is substantially pure leflunomide Form II.

Another aspect of the present invention provides novel leflunomide Form III. Leflunomide Form III is identifiable by its powder X-ray diffraction pattern that has characteristic peaks at 8.0, 9.8, 12.0, 13.4, 14.6, 16.1, 19.7, 21.9, 24.3, 25.4, 26.6 and 36.6°±0.2° at 2θ. Powder X-ray diffraction patterns were obtained using a Philips X-ray powder diffractometer, Goniometer model 1050/70 at a scanning speed of 2° per minute with Cu radiation (λ=1.5418 Å).

Figure 2:
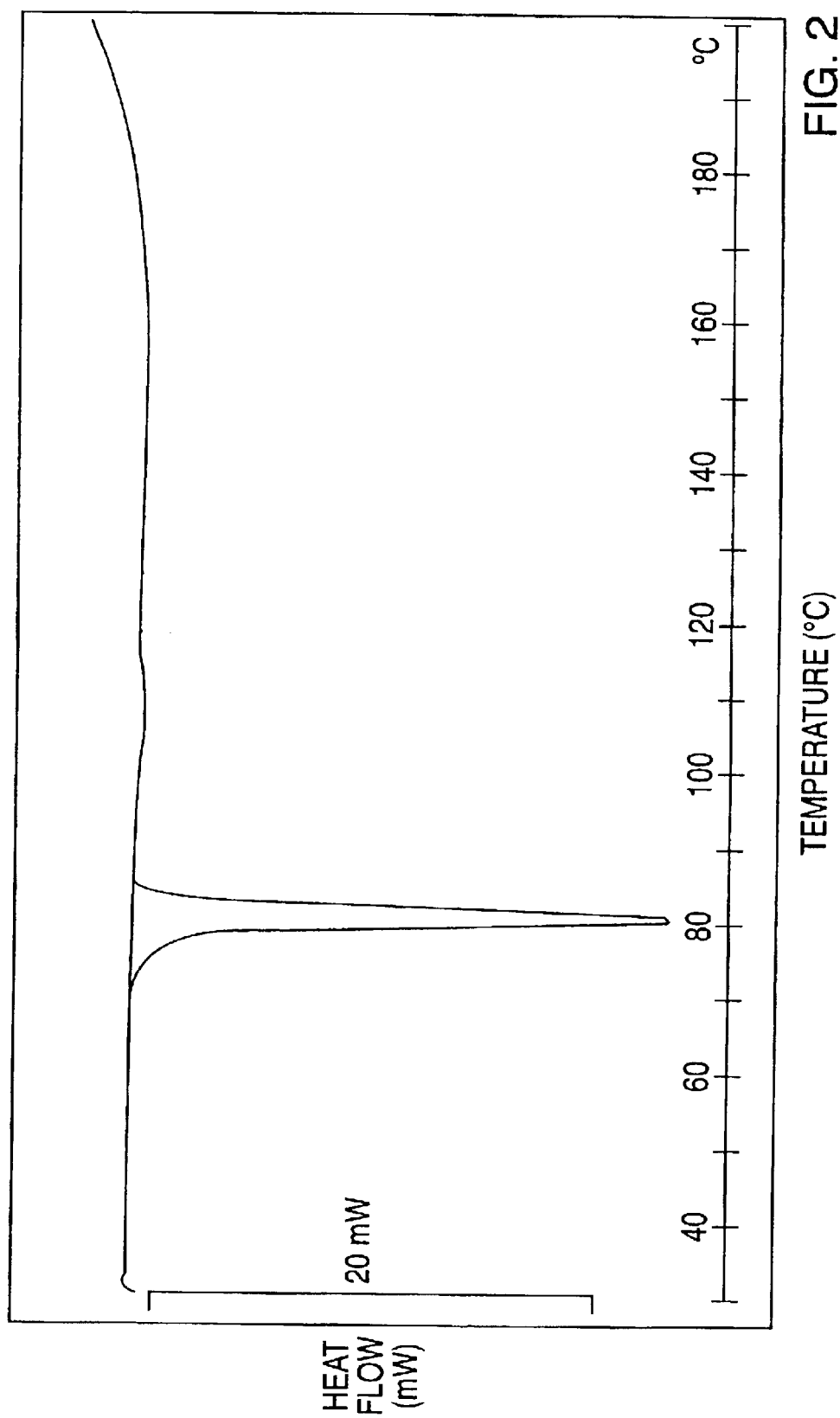
FIG. 2 is a characteristic DSC thermogram of leflunomide Form III.
Figure 3:
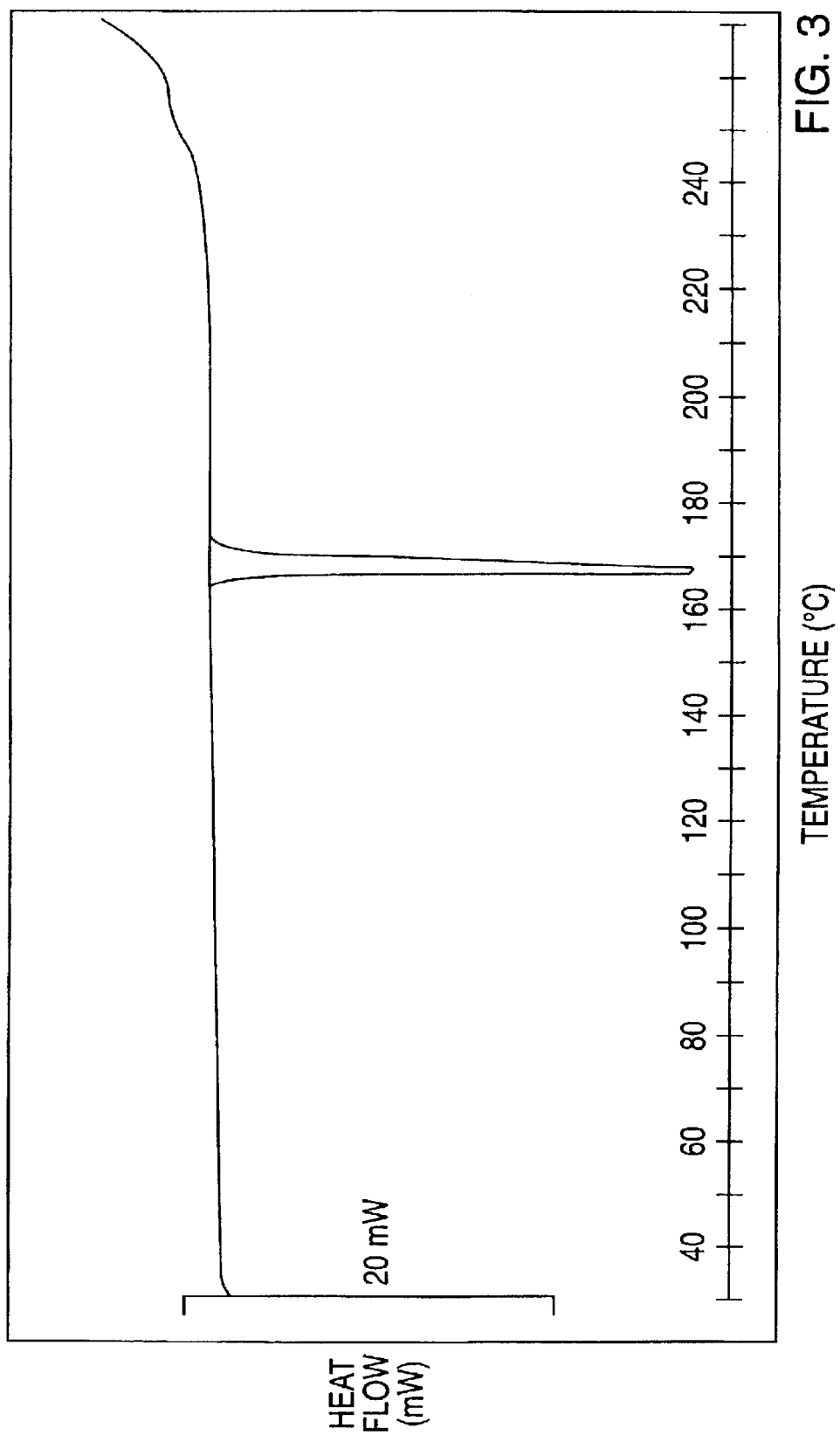
FIG. 3 is a characteristic DSC thermogram of leflunomide Form I.
Figure 4:
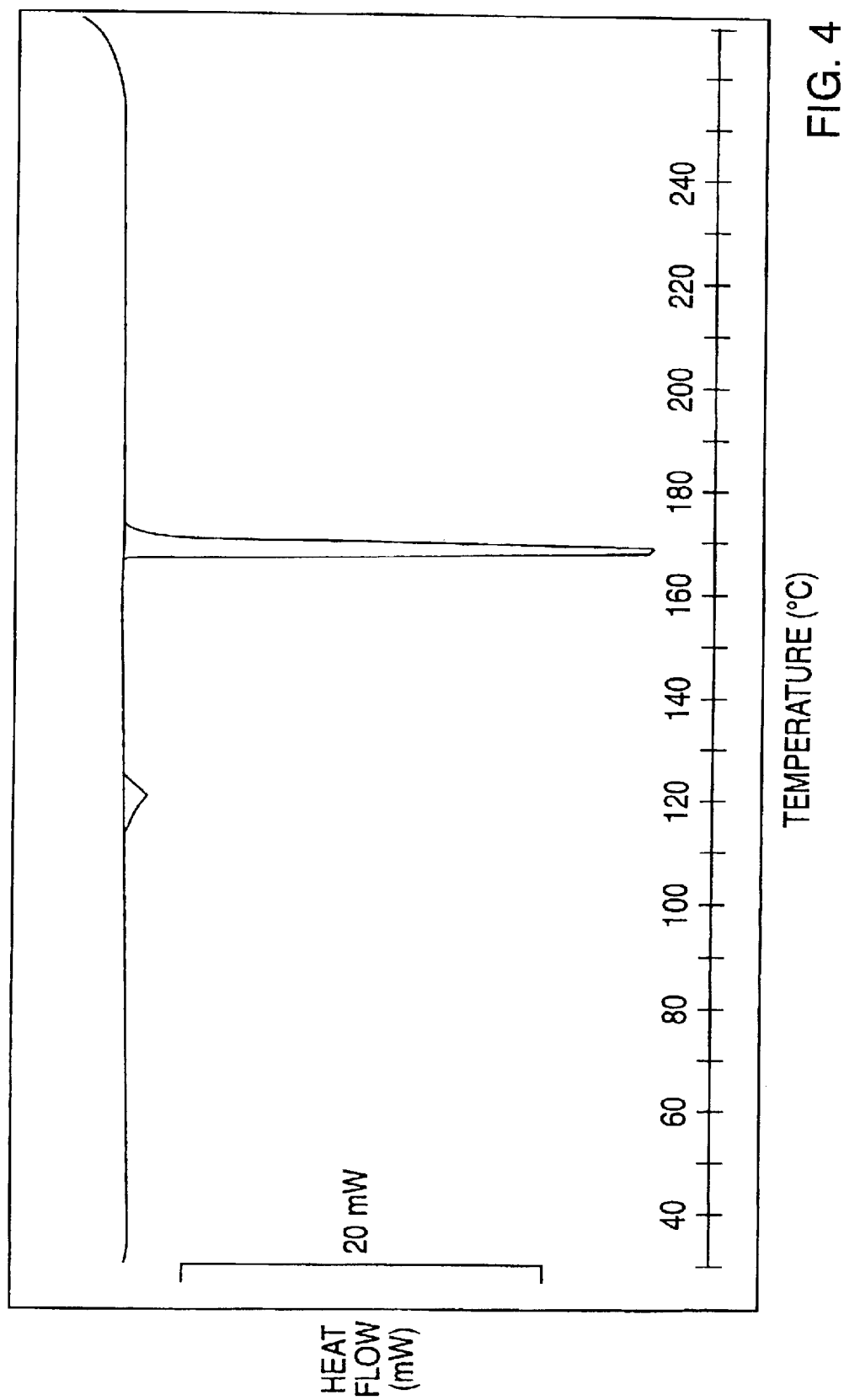
FIG. 4 is a characteristic DSC thermogram of leflunomide Form II.

Leflunomide Form III is also identifiable by its thermal properties. A DSC thermogram of leflunomide Form III at 10° C./min. shows only a sharp endothermic peak at 82° C. (See FIG. 2). For comparison, the DSC thermogram of Forms I and Forms II of leflunamide show a sharp endothermic peak at 167° C. (See FIGS. 3 and 4). The differential scanning calorimeter thermograms were obtained by methods known in the art using a DSC Mettler 821 Star°. Form III contains about 30% by weight solvent of crystallization and about 70% leflunomide. The presence of the solvent is not detectable by thermogravimetric analysis because the solvent is nonvolitile.

Leflunomide Form III is made generally according to the above-described method of making leflunomide Form II except that 2-pyrrolidone is used as the leflunomide solvent. By storing Form III at elevated temperatures, preferrably 40–80° C., more preferably about 60° C., for a prolonged period of time, preferably from about 12 hours up to several days, more preferably about two and a half days, Form III is transformed into Form I.

According to one process of making leflunomide Form III, 2-pyrrolidone is heated to from about 40° C. to about 70° C., more preferably about 50° C. to about 60° C. and most preferably about 55° C. and an amount of leflunomide is dissolved to give a nearly saturated leflunomide solution. One way to prepare a nearly saturated solution is to add an excess of leflunomide and after allowing sufficient time for the 2-pyrrolidone to become saturated with leflunomide, an additional amount of 2-pyrrolidone is added, preferably less than 10% of the original volume to dissolve the undissolved leflunomide. The hot solution also may be filtered to remove any undissolved leflunomide.

After obtaining the nearly saturated solution, the solution is then preferably allowed to cool to ambient temperature to crystallize leflunomide Form III. The crystals are then isolated by conventional means such as decanting, filtering or evaporating the solvent or any other method that separates the crystals from the bulk of the solvent. Following isolation, the crystals may be washed and/or dried.

According to another process for making leflunomide Form III, leflunomide is dissolved in an amount of 2-pyrrolidone to give a concentrated leflunomide solution. Dissolution may be performed advantageously at ambient temperature. A volume of water, preferably about one half to an equal amount with respect to 2-pyrrolidone, is added to the solution to induce crystallization. The crystals are then isolated by any method that separates the crystals from the bulk of the solvent. Following isolation, the crystals may be washed and/or dried.

The methods of isolating the crystals and other aspects of the processes for making leflunomide Form III are generally the same as the process for making leflunomide Form II of the present invention.

Leflunomide Form III is suitable for the treatment of acute immunological diseases such as sepsis, allergies, graft-versus-host disease and host-versus-graft disease; autoimmune disease like rheumatoid arthritis, systemic lupus erythematosis and multiple sclerosis; psoriasis, atopic dermatitis, asthma, urticaria, rhinitis, uveitis, type II diabetes, liver fibrosis, cystic fibrosis, colitis, and cancers. The present invention also provides pharmaceutical compositions and dosage forms containing leflunomide Form III suitable for use in the treatment of rheumatoid arthritis. Compositions may contain a pharmaceutically acceptable vehicle, i.e. one or more pharmaceutical excipients.

Compositions may have few or many excipients depending upon the dosage form used, the release rate desired and other factors. For example, compositions of the present invention may contain diluents such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents like calcium carbonate and dibasic calcium diphosphate and other diluents known to the pharmaceutical industry. Yet other suitable diluents include waxes, sugars and sugar alcohols like mannitol and sorbitol, lactose, lactose monohydrate and spray dried lactose, acrylate polymers and copolymers, as well as pectin, dextrin and gelatin. The diluents may also modify the release rate of the leflunomide from the composition.

Other excipients include tablet binders, such as povidone, acacia gum, pregelatinized starch, sodium alginate, glucose and other binders used in wet and dry granulation and direct compression tableting processes. Excipients that may also be present in a solid composition of leflunomide Form III further include disintegrants like sodium starch glycolate, crospovidone, low-substituted hydroxypropyl cellulose and others. Additional excipients include tableting lubricants like magnesium and calcium stearate, sodium stearyl fumarate and polyethylene glycol; flavorings; sweeteners; preservatives; pharmaceutically acceptable dyes; and glidants such as silicon dioxide and talc.

Whether used in pure form or in a composition, leflunomide Form III may be in the form of a powder, granules, aggregates or any other solid form. Leflunomide Form III may be used to make liquid compositions such as suspensions, syrups, elixirs, ointments, solutions and the like. Leflunomide Form III may also be used to prepare solid pharmaceutical compositions by blending, mixing, wet granulation, dry granulation or other methods.

Leflunomide Form III and compositions containing it may be presented to the patient in dosages. Dosages may be adapted for administration to the patient by oral, buccal, parenteral, ophthalmic, rectal and transdermal routes. Oral dosages include tablets, pills, capsules, troches, sachets, suspensions, powders, lozenges, elixirs and the like. Leflunomide Form III also may be administered as suppositories, ophthalmic ointments and suspensions, and parenteral suspensions. The most preferred route of administration of the leflunomide Form III is oral.

Capsule dosages, of course, will contain the solid composition within a capsule which may be made of gelatin or other encapsulating material. Tablets and powders may be coated. Tablets and powders may be coated with an enteric coating. The enteric-coated powder forms may have coatings comprising phthalic acid cellulose acetate, hydroxypropylmethyl cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

Preferred oral dosages of the present invention contain from about 20 mg to about 100 mg of leflunomide Form III or mixtures of Form III with other forms.

Having thus described the present invention with reference to certain preferred embodiments, the following examples are provided to further illustrate the processes by which leflunomide Forms II and III may be obtained. One skilled in the art will recognize variations and substitutions in the methods as described and exemplified which do not depart from the spirit and scope of the invention.

EXAMPLES

Preparation of Leflunomide Form II

Example 1
Crystallization of Form II from DMSO

DMSO (8 ml) was warmed to 50° C. Leflunomide (5.6 g) was added to the DMSO with stirring. After complete dissolution of the leflunomide, the stirred solution was allowed to cool to ambient temperature. Crystal formation was noted when the solution temperature reached 40° C. The mixture was stirred for another 30 minutes and then the crystals were isolated by filtration, washed with water and then dried under vacuum at 30° C. to give leflunomide Form II (3.4 g, 61%).

Example 2
Crystallization of Form II from DMSO/Water

Leflunomide (1.07 g) was dissolved in stirred DMSO (6 ml) at ambient temperature. Water (12 ml) was added dropwise to the stirred solution. The mixture was stirred for 30 minutes. The crystals which formed were isolated by filtration, washed with water and then dried under vacuum at room temperature to give leflunomide Form II (1 g, 93%).

Example 3
Crystallization of Form II from DME/Hexane

Leflunomide (6.1 g) was dissolved in DME (10 ml) at ambient temperature. Hexane (16 ml) was added to the stirred solution. The mixture was then stirred for about 30 min. after which time crystallization appeared to have ceased. The crystals were isolated by filtration through a paper filter and dried under vacuum at 30° C. to give leflunomide Form II (2.4 g, 39%).

Example 4
Crystallization of Form II from DMI/Water

Leflunomide (4.0 g) was dissolved in DMI (10 ml) at ambient temperature. Water (12.5 ml) was added to the stirred solution. The mixture was stirred for about 30 min. after which time crystallization appeared to have ceased. The crystals were isolated by filtration through a paper filter and dried under vacuum at 30° C. to give leflunomide Form II (3.1 g, 78%)

Examples 5–11
Crystallization of Form II from Mixtures of Other Solvents and Water Leflunomide Form II was obtained by the method of Example 4 from mixtures of other solvents and water in yields ranging from 29 to 82% as reported in Table I.

TABLE I

| Ex. No. | Leflunomide (g) | Solvent | (ml) | Anti-solvent | (ml) | Form II (g) | % Yield |
|---|---|---|---|---|---|---|---|
| 5 | 5.6 | Acetone | 10 | Water | 6 | 2.3 | 41 |
| 6 | 1.7 | MeOH | 10 | Water | 1.5 | 0.75 | 44 |
| 7 | 1.3 | Dioxane | 10 | Water | 8 | 0.9 | 69 |
| 8 | 11 | DMF | 10 | Water | 6 | 9 | 82 |
| 9 | 2.8 | DME | 10 | Water | 9.3 | 1.1 | 39 |
| 10 | 1.9 | EtOAc | 10 | Water | 26 | 0.55 | 29 |
| 11 | 0.8 | IPA | 11 | Water | 15 | 0.4 | 50 |

Example 12
Crystallization of Form II from 2-Ethoxy Ethanol

Leflunomide (5.6 g) was dissolved in 2-ethoxy ethanol (10 ml) at 60° C. The resulting solution was allowed to cool to an ambient temperature of 20° C. Crystals were isolated by filtration and dried at 30° C. under vacuum to give leflunomide Form II (1.6 g, 29%)

Preparation of Leflunomide Forms III and I

Example 13
Crystallization of Form III from 2-Pyrrolidone and Transformation of Form III into Form I 2-Pyrrolidone (10 ml) was heated to 55° C. and leflunomide (10 g) was added with stirring. After dissolution was complete, the solution was allowed to cool to ambient temperature. After about an hour the mixture was filtered through a paper filter. After drying under vacuum at ambient temperature, 8 g (80%) of leflunomide Form III was obtained.

Form III was stored in an open container under vacuum for two and a half days at 60° C., after which time it had converted into leflunomide Form I.

Example 14
Crystallization of Form III from 2-Pyrrolidone/Water

2-Pyrrolidone (5 ml) was heated to about 40° C. and leflunomide (1 g) was added with stirring. After dissolution was complete, the solution was allowed to cool to ambient temperature. Water (3 ml) was added to the stirred solution. The crystals were isolated by filtration, washed with water (3 g) and dried at ambient temperature under vacuum to a constant weight. Leflunomide (1 g, 100%) was recovered as crystalline Form III.

We claim:

1. A process for preparing leflunomide Form I comprising the steps of
   a) heating crystals of leflunomide Form III for a period of time sufficient to transform the Form III crystals into leflunomide Form I and
   b) recovering crystals of leflunomide Form I.

2. The process of claim 1 wherein the crystals of leflunomide Form III are heated to a temperature of between 40 and 80° C.

3. The process of claim 2 wherein the crystals of leflunomide Form III are heated to a temperature of about 60° C.

4. The process of claim 1 wherein the crystals of leflunomide Form III are heated for a period of from about twelve hours to about three days.

5. The process of claim 4 wherein the crystals of leflunomide Form III are heated for a period of from about two to about three days.

6. The process of claim 1 wherein the crystals of leflunomide Form III are heated under reduced pressure.

* * * * *